United States Patent
Ehrhardt et al.

(10) Patent No.: US 8,017,823 B2
(45) Date of Patent: Sep. 13, 2011

(54) PROCESS FOR THE MANUFACTURE OF ACETYLENE BY PARTIAL OXIDATION OF HYDROCARBONS

(75) Inventors: Kai Rainer Ehrhardt, Speyer (DE); Raymond Poche, Prairieville, LA (US); William R. Scullin, Baton Rouge, LA (US); Michael L. Hayes, Gonzales, LA (US)

(73) Assignee: BASF, SE (DE)

( * ) Notice: Subject to any disclaimer, the term of this patent is extended or adjusted under 35 U.S.C. 154(b) by 1315 days.

(21) Appl. No.: 11/402,326

(22) Filed: Apr. 11, 2006

(65) Prior Publication Data
US 2007/0238910 A1 Oct. 11, 2007

(51) Int. Cl.
*C07C 4/02* (2006.01)
*C07C 2/02* (2006.01)

(52) U.S. Cl. ........ 585/539; 585/537; 585/538; 585/540; 585/921; 585/922; 700/41; 700/42; 700/43; 700/50; 415/1; 364/148

(58) Field of Classification Search .................. 364/148; 415/1; 585/537, 538, 539, 540, 921, 922; 700/42, 41, 43, 50
See application file for complete search history.

(56) References Cited

U.S. PATENT DOCUMENTS

| 5,706,193 A | * | 1/1998 | Linzenkirchner | ............... 700/42 |
| 5,824,834 A | | 10/1998 | Bachtler et al. | |
| 6,164,901 A | * | 12/2000 | Blotenberg | ...................... 415/1 |

FOREIGN PATENT DOCUMENTS

DE 101 01 511 A1 * 9/2002

OTHER PUBLICATIONS

*Ullmann's Encyclopedia of Industrial Chemistry*, Fifth, Completely Revised Edition, vol. A1, Abrasives to Aluminum Oxide, "BASF Process (Sachsse-Bartholomé)", Section 4.2.1., pp. 97-145 (2000).

* cited by examiner

*Primary Examiner* — Prem C Singh
(74) *Attorney, Agent, or Firm* — Connolly Bove Lodge & Hutz

(57) ABSTRACT

A process is proposed for continuously operating a plant for preparing acetylene from hydrocarbons by partial oxidation, cleavage in an arc or pyrolysis of hydrocarbons to obtain a reaction gas mixture which is conducted through one or more compressors, the pressure of the reaction gas mixture on the suction side of the compressor being controlled within a predefined range by means of a conventional controller, which comprises additionally using a high-level model-supported predictive controller which reacts to abrupt changes in the mass flow rate of the reaction gas mixture.

6 Claims, 1 Drawing Sheet

PROCESS FOR THE MANUFACTURE OF ACETYLENE BY PARTIAL OXIDATION OF HYDROCARBONS

The present invention relates to a process for preparing acetylene from hydrocarbons by partial oxidation, cleavage in an arc, cleavage in a plasma or pyrolysis of hydrocarbons or carbon.

Acetylene is prepared Industrially by processes including that developed by BASF, which is based on partial oxidation of hydrocarbons with oxygen. It is described in detail in "Ullmann's Encyclopedia of Industrial Chemistry, Sixth Edition, 2000, Electronic Release, Chapter 4.2.1".

The two feedstock streams—the stream comprising the hydrocarbon (generally typically saturated, readily evaporable hydrocarbons, alkanes usually up to C10 in chain length, preferably natural gas) on the one hand and the Stream comprising the oxygen on the other hand—are first preheated to from approx. 200° C. to 650° C. The preheating temperature is dependent upon the hydrocarbon used. Typically, it is heated up to the order of magnitude of the ignition temperature of the hydrocarbon. In the case of use of natural gas, the preheating temperature is typically in a range of from about 500° C. to 650° C. The two streams are then mixed and only then reacted in the firing chamber in a flame, which is stabilized by the so-called burner block.

Preheating and premixing in conjunction with a subsequent flame reaction form the basic idea of the BASF process for partial oxidation of hydrocarbons with oxygen to prepare acetylene. As a result of this process, the reaction rate of the oxidation of the hydrocarbons becomes independent of the mixing rate of the stream. In this way, the residence time in the reaction zone can be reduced to values which are substantially smaller than the half-life of the thermally unstable acetylene. Accordingly, the process can substantially increase the acetylene yields.

The premixing has to be effected rapidly and with prevention of backflow, since the mixture otherwise self-ignites owing to the high preheating in such a case, the flame does not burn in the firing chamber but rather in the premixing zone and has to be extinguished, for which nitrogen is added and the oxygen feed to the reactor is interrupted. The gas which flows through the reactor up to reignition of the flame and compliance with the specifications after ignition is flared off.

The flame reaction at temperatures above about 1500° C. is quenched after a few milliseconds by injecting water or oil, i.e. the very rapid cooling to, for example, 90° C. or 220° C. terminates the free-radical chain reaction in the flame. This prevents the degradation of the thermally unstable acetylene intermediate. After very long residence times (greater than approx. 1 second), it would be virtually impossible to obtain any acetylene. The reaction product is the so-called cleavage gas which is a mixture of acetylene, crude synthesis gas (mainly $H_2$ and CO), steam and by-products, especially soot, and also higher hydrocarbons.

An improvement in the process with water quench is described inn U.S. Pat. No. 5,824,834, which describes a process which works with a closed water quench circuit. This prevents contact of the process water polluted with harmful substances with the atmosphere.

The cleavage gas obtained is subsequently compressed and then separated in a known manner. In principle, there is a permissible operating range for the pressure at the inlet Into the compression, which is laid down, for example, by the design of the apparatus or the safety concept. When the suction pressure leaves the permissible range, circuits are triggered. For example, in the BASF process, the suction process is controlled for safety reasons within a range which is always greater than ambient pressure, and the compressors are shut down at too low a pressure. Analogously, one or more reactors are shut down at too high a suction pressure.

For the equalization of small variations in the mass flow rate of the reaction gas mixture, a conventional controller, for example a PID controller with slow control characteristic, can be used to keep the suction pressure constant. Preference is given to the slow control characteristic to prevent control oscillations which have an adverse effect on the subsequent process stages in the course of normal operation.

The failure of a reactor, for example caused by premature ignition or failure of a compressor, results in abrupt massive changes in the mass flow rate of the reaction gas mixture. These cannot be controlled by the conventional controllers with slow control characteristic, so that the suction pressure leaves the permissible range, which in turn leads to the shutdown of further plant parts and, In the worst case, even to complete shutdown of the plant.

The problem outlined above occurs especially in modem plants for preparing acetylene, in which the volume of the apparatus which can buffer changes in load has been distinctly reduced because, in particular, electrostatic filters for separating out soot are no longer provided since the task, as described in U.S. Ser. No. 60/775,158, is assumed by the compressor, and because the capital costs for a gasometer are to be avoided.

SUMMARY OF THE INVENTION

It was thus an object of the present invention to ensure the continuous operation of a plant for preparing acetylene, even at high mass flow rates to be processed. In particular, continuous operation should also be ensured for plants with low buffer volume, especially owing to absence of electrostatic filters for soot separation and of a gasometer for the gas to be compressed.

The solution consists in a process for continuously operating a plant for preparing acetylene from hydrocarbons by partial oxidation, cleavage in an arc or pyrolysis of hydrocarbons to obtain a reaction gas mixture which is conducted through one or more compressors, the pressure of the reaction gas mixture on the suction side of the compressor being controlled within a predefined range by means of a conventional controller, which comprises additionally using a higher-level model-supported predictive controller which reacts to abrupt changes in the mass flow rate of the reaction gas mixture.

Figure 1:
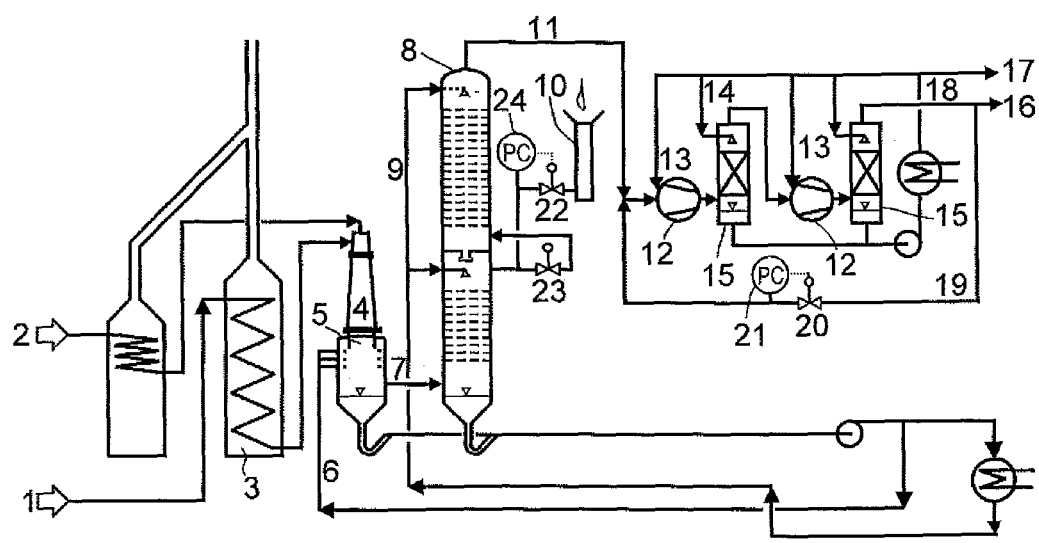
FIG. 1 shows the schematic illustration of a preferred plant for carrying out the process according to the invention.

The invention is not restricted with regard to the specific performance of the process: what is essential is that a reaction mixture is obtained and is conducted through at least one compressor.

For example, it may be a process as described in U.S. Ser. No. 60/775,158, in which it is possible to dispense with wet electrostatic filters, which may be a frequent cause of interruptions to operation.

According to the invention, for the control of the pressure of the reaction mixture on the suction side of the compressor, in addition to the conventional controller with slow control characteristics, a higher-level model-supported predictive controller is used which reacts to abrupt changes in the mass flow rate of the reaction gas mixture. Abrupt changes in the mass flow rate of the reaction gas mixture may be quasi-instantaneous changes in the mass flow rate of the reaction gas mixture, by more than 5%, preferably more than 10% or else by more than 50% thereof.

The pressure of the reaction gas mixture on the suction side of the compressor can preferably be controlled by the recycling of compressed gas to the suction side by means of a control unit, in particular one or more control valves, vanes or flaps which are controlled by the conventional controller.

In the case of appropriate technical modification, the pressure, of the reaction mixture on the suction side of the compression can additionally be controlled by the speed of the compressor which reduces the mass flow rate of the reaction gas mixture returned on average.

In the event of a disruption to operation, in particular the failure of a reactor, which leads to a quasi-instantaneous decrease in the mass flow rate of the reaction gas mixture, the pressure of the reaction gas mixture on the suction side of the compressor is controlled by the higher-level model-supported predictive controller which calculates the decrease in the mass flow rate of the reaction gas mixture and uses the characteristic thereof to actuate a control unit, so that reaction gas mixture is returned from the pressure side to the suction side of the compressor.

Model-supported predictive controllers are known and are based on forecasting the future course of the control parameter and of the control difference over a predefined time prediction range of the basis of the values measured up to the current time and stored historical values.

The higher-level model-supported predictive controller preferably continually calculates the produced mass flow rate of the reaction gas mixture, in particular as a multiple of the mass flow rate of hydrocarbons used in the process for preparing acetylene by partial oxidation.

The higher-level model-supported predictive controller preferably determines the reduced mass flow rate of reaction gas mixture which corresponds to the increased recycling of compressed reaction gas mixture to the suction side of the compressor as the difference of the calculated mass flow rate before and after the start of the disruption.

In particular, the higher-level model-supported predictive controller adjusts the position of the control unit using the calculated, reduced mass flow rate of the reaction gas mixture, the current position of the control unit and the characteristic of the control unit, measures the parameter and uses this function of the higher-level model-supported predictive controller to modify the control signal of the control unit so as to compensate for the disruptive influence.

In addition, after the intervention of the higher-level model-supported predictive controller, the conventional controller and/or the speed controller of the compressor can correct any control difference remaining, which can result from the finite precision of the calculations.

In the event of failure of one compressor in a plant comprising two or more compressors connected in parallel, the higher-level model-supported predictive controller can calculate the reduced mass flow rate of compressed reaction gas mixture and divert a corresponding mass flow rate of the reaction gas mixture from the suction side of the compressor out of the plant, in particular to a flare or to a power station.

In particular, the mass flow rate, diverted from the suction side of the compressor out of the plant, of the reaction mixture is adjusted by means of a control unit, in particular a valve, a vane or a flap, and the required position of the control unit in the event of occurrence of disruption is adjusted by the higher-level modes supported predictive controller using the calculated difference, the current position of the valve and the characteristic.

The higher-level model-supported predictive controller used in the present process is preferably a feed-forward controller.

The process according to the invention has the advantage that it ensures continuous operation of plants for preparing acetylene in an effective manner which is simple from a process technology point of view, especially also for plants with large capacity but restricted buffer volume, especially owing to absence of electrostatic filters for soot separation and of the gasometer. By avoiding shutdown of the plant, interruption to production in a multitude of additional affected up- and downstream plants is also prevented. Apparatus wear by startup and shutdown operations, especially of the compressors, is reduced.

As a result of the intervention of the higher-level model-supported predictive controller, disruptions are detected reliably and the spreading of the Initial disruption is thus prevented. As a result of this, it is also possible to adjust the conventional PID controller to act more slowly than without a higher-level controller, which makes normal operation smoother.

The invention will be illustrated hereinafter with reference to a drawing.

The sole FIGURE shows the schematic Illustration of a preferred plant for carrying out the process according to the invention.

The feedstocks natural gas 1 and oxygen 2 are preheated in fired preheaters 3, mixed in the mixing zone 4 and reacted in a flame reaction in the firing chamber 5. The flame is quenched below the firing chamber by Injecting process water. The acetylene-comprising reaction mixture, the so-called cleavage gas 7, enters the cooling column 8 with approximately cooling limit temperature and saturated with steam. There, the cleavage gas is cooled with the aid of cooled process water which condenses a majority of the steam. The flare 10 is required for startup and shutdown operations and for operational interruptions which are caused, for example, by premature ignition. From the cooling column 8, cleavage gas 11, cooled to 40° C. for example, is drawn off and subsequently compressed from 1.1 to 11 bar absolute by means of a two-stage screw compressor 12 with water Injection 13. Downstream of each compression stage, the cleavage gas is cooled, to 40° C. for example, by means of cooled process water 14 in cooling columns 15. The compressed cleavage gas 16 is subsequently separated Into its constituents, as described, for example. In the text passages cited at the outset from Ullmann's Encyclopedia of Industrial Chemistry, Sixth Edition, 2000, Electronic Release, Chapter 4.2.1.

If the screw compressors run at constant speed, the difference between the amount of cleavage gas compressed (stream 18) and the amount of cleavage gas drawn off from the plant (stream 16) is to be returned to the suction side of the compressors 12 (steam 19). The amount recycled is controlled by means of the conventional pressure controller with slow control characteristic 21 and the control valve 20.

If the screw compressor 12 has a speed control, the performance can be minimized by adjusting the delivery rate (stream 18) using the compressor speed. However, speed control systems are slow, which is why an additional pressure control is indispensable.

In the event of a disruption to operation in which the flame flashes back from the firing chamber 5 into the mixing cell 4 or the hydrocarbon-oxygen mixture self-ignites in the mixing zone, the flame is extinguished by interrupting the $O_2$ feed (stream 2) and $N_2$ addition and the gas is sent to the flare 10. To this end, flare vane 22 opens and plant vane 23 closes. This has the consequence that the amount of cleavage gas fed via the compressors 12 (stream 11) decreases virtually instantly, so that the amount of cleavage gas returned (stream 19) has to be increased correspondingly. Without the rapid intervention of the control valve 20, the pressure of the cleavage gas on the suction side of the compressor (stream 11) would decrease rapidly, the speed of the pressure reduction depending upon the cleavage gas volume flow rates and the volume of the apparatus and pipelines upstream of the compression. The raped pressure drop can trigger a pressure circuit which shuts down one or both compressors 12 when the pressure decreases into a range below the predefined range.

The failure of a compressor, which is triggered, for example, by circuits, leads to an abrupt change in the cleavage gas volume flow rate (stream 18), which is why the suction-site cleavage gas pressure of the stream 11 rises rapidly without countermeasures. When this pressure exceeds a critical value, reactors have to be shut down.

It can easily be seen that disruptions can spread. For example, a burner failure can lead to an impermissible pressure drop which causes the shutdown of a compressor. The pressure can then rise impermissibly, which causes the shut-off of further burners. Ultimately, a total shutdown of the plant which leads to considerable economic damage is possible in this way as a result of a comparatively limited initial disruption.

For the control of this quasi-instantaneous initial disruption, which cannot be accomplished by the conventional slow controller and which, owing to the reduced buffer volume as a result of absence of a gasometer between, for example, cooling column 8 and compressor 12, also cannot be absorbed, a higher-level feed-forward control is provided by way of example in accordance with the invention. This is provided in addition to the conventional pressure controller 21 at the same point in the plant and is therefore not shown additionally; in the figure. The higher-level feed-forward controller continually calculate the amount of cleavage gas (stream 11) from the amount of natural gas supplied (stream 1), taking into account whether the gas from individual reactors is sent to compression or to the flare 10. The calculation takes account of the specific composition of the hydrocarbon stream used, the ratio of oxygen to hydrocarbon stream, and temperature and pressure of the steam-saturated cleavage gas.

When the cleavage gas of one reactor, for example owing to premature ignition, is quasi-instantaneously no longer available for compression, the higher-level feed-forward controller calculates the difference as detailed above. In accordance with the current position of the control valve 20, the characteristic thereof and the calculated difference in the amounts of cleavage gas before and after the disruption, the new valve opening of the control valve 20 is calculated and set directly. Thereafter, the pressure control is taken over again by the conventional, slow pressure controller.

When a compressor fails, the excess amount of cleavage gas is calculated analogously and the flare vane 22 is likewise opened in a controlled manner. Thereafter, the pressure control is taken over again by the conventional slow pressure controller 24. In addition to the delivery volume of the compressor at nominal speed, the calculation of the compressed amount of cleavage gas takes account of the current compressor speed when this is variable. When temperature and pressure at the Inlet of the compressor and of the flare differ significantly, this should also be taken into account in the calculation. Moreover, it may, depending on the compressor design, be necessary to take into account all further parameters which significantly influence the delivery rate, i.e. significantly shift the characteristic. One example of turbocompressors might be the pressure downstream of compression.

What is claimed is:

1. A process for continuously operating a plant for preparing acetylene from hydrocarbons by partial oxidation to obtain a reaction gas mixture which is conducted through one or more compressors, the pressure of the reaction gas mixture on the suction side of the compression being controlled within a predefined range by means of a controller, which comprises additionally using a higher-level model-supported predictive controller which reacts to abrupt changes in the mass flow rate of the reaction gas mixture, and, wherein the plant comprises two or more compressors connected in parallel and the higher-level model-supported predictive controller calculates the reduced mass flow rate of compressed reaction gas mixture in the event of failure of one compressor or a plurality of compressors and diverts a corresponding mass flow rate of the reaction gas mixture from the suction side of the compression out of the plant.

2. The process according to claim 1, wherein the mass flow rate, diverted from the suction side of the compressor out of the plant, of the reaction mixture is adjusted by means of a control unit and the required position of the control unit in the event of occurrence of disruption is adjusted by the higher-level model-supported predictive controller using the calculated difference, the current position of the valve and the characteristic.

3. The process according to claim 1, wherein the higher-level model-supported predictive controller calculates the compressed mass flow rate of the reaction gas mixture from the characteristic of the compressor and all parameters which influence the characteristic.

4. The process according to claim 1, wherein the higher-level model-supported predictive controller diverts a corresponding mass flow rate of the reaction gas mixture from the suction side of the compression out of the plant to a flare or to a power station.

5. The process according to claim 4, wherein the higher-level model-supported predictive controller calculates the mass flow rate of the reaction gas mixture to be diverted out of the plant according to pressure and temperature at the inlet of the compressor and the flare and from the compressed mass flow rate of the reaction gas mixture.

6. The process according to claim 1, wherein the higher-level model-supported predictive controller calculates the compressed mass flow rate of the reaction gas mixture from the characteristic of the compressor and all parameters which influence the compressor speed.

* * * * *